United States Patent [19]

Foody

[11] Patent Number: 4,735,209

[45] Date of Patent: Apr. 5, 1988

[54] STERILIZABLE APPLANATION TONOMETER

[76] Inventor: Robert J. Foody, 517 S. Grove, Oak Park, Ill. 60304

[21] Appl. No.: 2,727

[22] Filed: Jan. 13, 1987

[51] Int. Cl.$^4$ ............................................. A61B 3/16
[52] U.S. Cl. ................................. 128/652; 250/455.1
[58] Field of Search ............................... 128/645–652; 73/78–79, 81; 250/431, 455.1

[56] References Cited

U.S. PATENT DOCUMENTS

| | | | |
|---|---|---|---|
| 3,070,997 | 1/1963 | Papritz et al. | 128/652 |
| 3,452,589 | 7/1969 | Hargens et al. | 128/645 |
| 3,511,085 | 5/1970 | Posner | 128/652 |
| 3,913,390 | 10/1975 | Piazza | 128/652 |
| 4,209,021 | 6/1980 | Warming | 128/652 |
| 4,621,644 | 11/1986 | Eilers | 128/652 |
| 4,624,235 | 11/1986 | Krabacher et al. | 128/652 |
| 4,628,938 | 12/1986 | Lee | 128/652 |

FOREIGN PATENT DOCUMENTS 2307733 8/1974 Fed. Rep. of Germany ...... 128/645

Primary Examiner—Kyle L. Howell
Assistant Examiner—Angela D. Sykes
Attorney, Agent, or Firm—Neuman, Williams, Anderson & Olson

[57] ABSTRACT

Sterilization of the corneal contact surface in an applanation tonometer is facilitated by an apparatus comprising a pivotable housing for the corneal contact surface of a corneal applanation device whereby the corneal contact surface may be rotated into a sterilization position without disassembly of the tonometer. In another embodiment, a cup for holding a sterilizing medium is provided for sterilizing the corneal contact surface in the sterilization position.

11 Claims, 1 Drawing Sheet

STERILIZABLE APPLANATION TONOMETER

FIELD OF THE INVENTION

The invention is in the field of applanation tonometry and particularly relates to improvements in an apparatus for supporting and facilitating sterilization of the corneal contact surface of an applanation tonometer.

BACKGROUND OF THE INVENTION

The measurement of the intraocular pressure is an important diagnostic tool for the identification of eye disorders, especially glaucoma. Tonometry is routinely used to screen the population at large and to track persons with known pathology. For more than two decades, the Goldmann tonometer has been a standard in the art of tonometry. See U.S. Pat. No. 3,070,997 patented Jan. 1, 1963.

Using the Goldmann apparatus, the intraocular pressure is measured by flattening or applanating a standard area of the cornea to conform to a planar corneal contact surface of a corneal applanation device placed in contact with the cornea. This method, known as applanation tonometry, employs a circular transparent plane surface, or corneal contact surface, of known diameter which is urged against the cornea while an observer views the degree of applanation of the cornea through the corneal contact surface with the aid of a slit lamp or similar light source and a small quantity of fluorescein placed in the lacrimal fluid. The medical observer adjusts the force applied to the corneal contact surface until the applanated area of the cornea just conforms to a predetermined standard area defined by the corneal contact surface, at which point the force urging the surface against the cornea and determining the intraocular pressure is recorded.

In the prior art devices, the corneal contact surface must be sterilized for each use. This is desirable because infection and disease may possibly be transmitted through lacrimal fluid, and each measurement of the intraocular pressure requires that the corneal contact surface be brought into physical contact with the cornea for an interval ranging from a few seconds to a minute or more. A disadvantage of the prior art tonometers was that the corneal applanation device including the corneal contact surface had to be physically removed from the tonometer after each use for sterilization.

Other patents describing various applanation tonometers are U.S. Pat. Nos. 4,621,644; 4,624,235 and 4,628,938.

OBJECTS OF THE INVENTION

One object of the invention is to provide an improved applanation tonometer apparatus to facilitate sterilization of the corneal contact surface in an applanation tonometer by the physical diversion of the corneal contact surface from a measuring plane into a sterilization plane. A second object is to provide a method using said apparatus to provide a sterile corneal contact surface without removal of the corneal contact surface from the tonometer apparatus.

BRIEF SUMMARY OF THE INVENTION

In one form the present invention is an improved apparatus for facilitating sterilization of the corneal contact surface of an applanation tonometer, which includes a corneal applanation device comprising a tubular body having a planar corneal contact surface at one end thereof for bearing against a cornea, a housing for supporting said tubular body, a base for supporting said housing, and connecting means for connecting said housing to said base and allowing said housing to pivot about said base.

It should be understood that the drawings are not necessarily to scale and that the embodiments are sometimes illustrated by phantom lines and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE INVENTION

Figure 1:
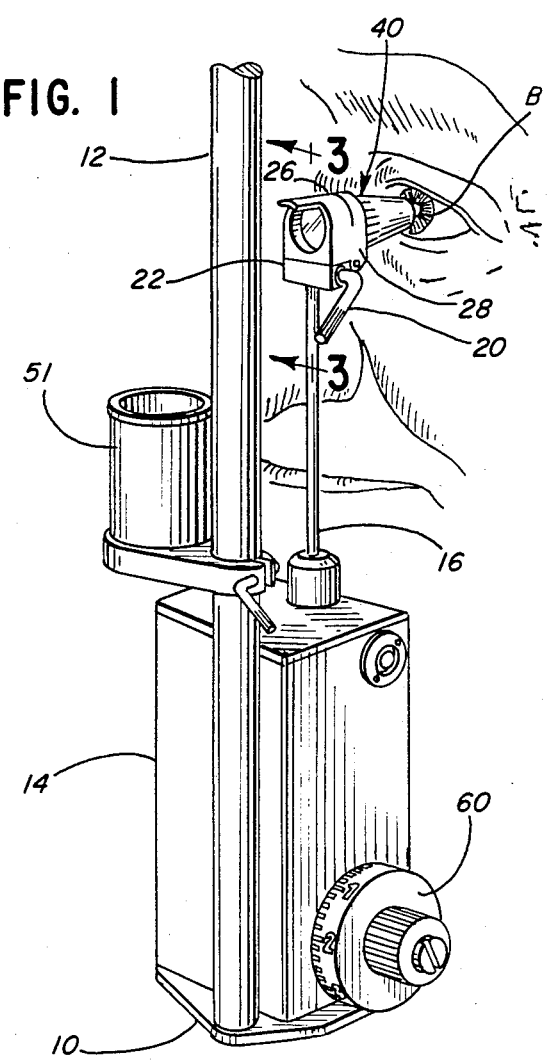
FIG. 1 is a perspective view of the invention in a measuring position in cooperation with the other elements of an applanation tonometer.
Figure 2:
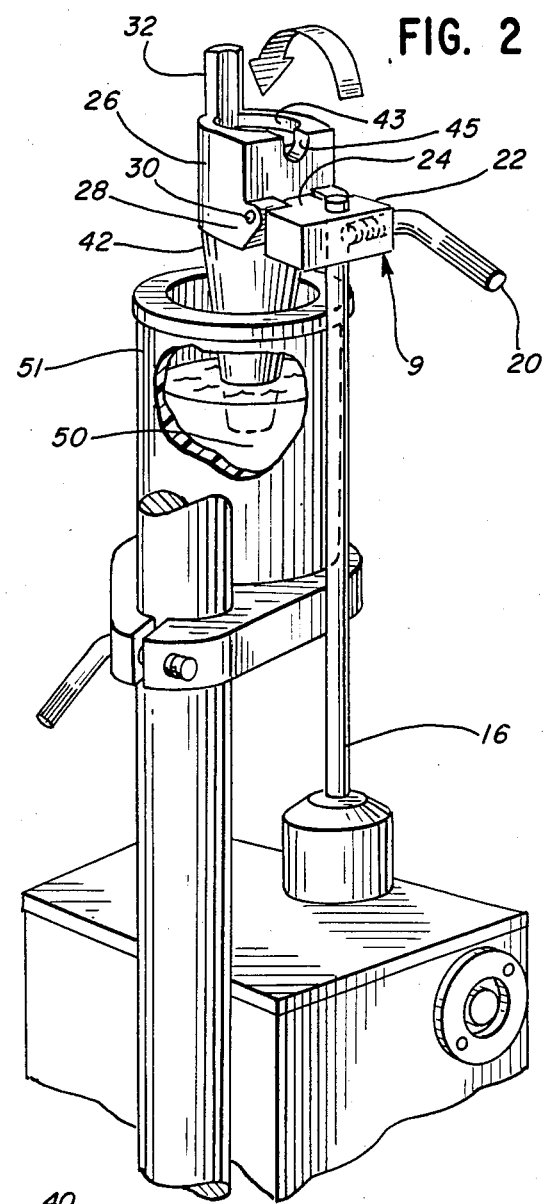
FIG. 2 is a perspective view of the invention in a sterilization position in cooperation with the other elements of an applanation tonometer.

Referring to the attached drawing, the tonometer shown in FIGS. 1 and 2 has a frame 10, said frame being adapted to be connected to and carry a slit lamp microscope (not shown) or similar device by an arm 12. A pressure measuring system 14 also rests on and is carried by the frame 10. The free end of a lever 16, generally rod-like in shape, extends out of the pressure measuring system 14 to a corneal applanation device 40 in a hinged mounting 9 secured to the lever 16. The lever 16 is free to rotate about its own axis.

Figure 3:
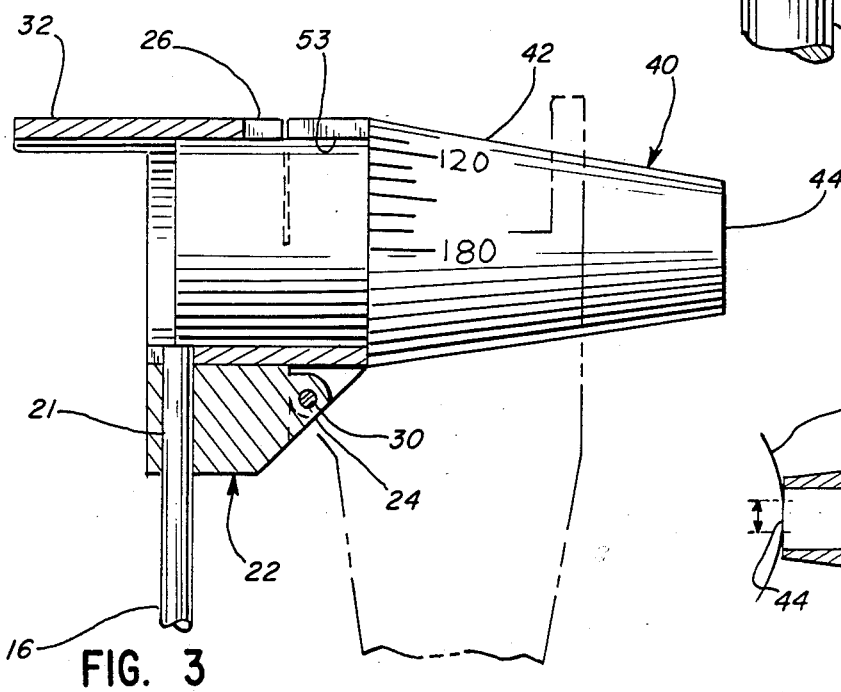
FIG. 3 is a side elevation view in partial cross section of a preferred embodiment of the invention.

The free end of the lever 16 is secured by a set screw 20 in an aperture 21 formed in a base 22 of the mounting 9. The base 22 further comprises an integral pivot means 24 as depicted in FIG. 2 and shown in cross section in FIG. 3. A housing 26 having an integral pivot means 28 operates in cooperation with the base 22 and its pivot means 24 through a pivot pin 30 as illustrated by the phantom lines in FIG. 3. In a preferred embodiment of the invention, the housing 26 has an integral handle 32 for facilitating manual rotation of the housing 26 around the pivot pin 30.

A corneal applanation device 40 comprising a tubular body 42 usually made of material such as glass or plastic is closed at its one outer end to form an optically transparent corneal contact surface 44, said body 42 being frictionally held in a bore 43 formed in the housing 26. In a preferred embodiment, the housing 26 has formed therein an aperture or notch 45 such that the housing 26 and its associated base 22 are capable of a range of vertical adjustment on the lever 16 which could, except for notch 45, be limited by housing 26. This feature of the invention allows for the proper fine vertical alignment of the corneal contact surface 44 of device 40 in housing 26 carried on rod 16 with the slit lamp microscope or other similar light source.

Further, in accordance with the invention a sterilizing medium 50 or means is provided in close proximity (contained for example, in a cup 51) to the corneal contact surface 44 so that the corneal contact surface 44 may be brought into contact with the sterilizing medium 50 by rotating the housing 26 and the corneal applanation device 40 horizontally and downwardly with respect to the axes of the pivot pin 30 and the lever 16. In a preferred embodiment of the invention, the sterilizing medium 50 is a sterilizing oxidizing solution, such as hydrogen peroxide. It should be understood that the invention is not necessarily limited to this particular embodiment. Other sterilizing means, for example, ultraviolet radiation, or other sterilizing solutions, are considered to be equivalents within the scope of the invention and may also be used.

In operation, the corneal applanation device 40 and housing 26 are initially in a closed or horizontal measuring position with respect to the base 22 as depicted in FIG. 1. The corneal contact surface 44 on the outer end of the corneal applanation device 40 is directed towards the cornea B by rotating the lever 16 through manipulation of the handle 32. The corneal contact surface 44 is then urged against the cornea B by a measured force applied through the manipulation of a calibrated control dial 60 and transmitted through the lever 16. An observer views the flattened or applanated area of the cornea through the corneal contact surface 44 with the aid of a slit lamp or similar light source and a small quantity of fluorescein placed in the lacrimal fluid. The observer adjusts the force applied to the corneal contact surface 44 by manipulating the calibrated control dial 60 of the control system 14 until the applanated area of the cornea B corresponds to a standard area defined by the corneal contact surface 44, at which point the force urging the corneal contact surface 44 against the cornea B is recorded.

The corneal contact surface 44 is then withdrawn from the cornea B. The housing 26 and associated corneal applanation device 40 are hingedly manipulated around the pivot pin 30 and the axis of the lever 16 by means of the handle 32 to bring the corneal applanating device 40 into a vertical sterilizing position in contact with a sterilizing medium 50 as shown in FIG. 2. The corneal contact surface 44 is sterilized by contact with a sterilizing medium 50 until sterilization has been effected. Finally, the corneal applanating device 40 is returned to a horizontal measuring position as illustrated in FIG. 1 by manipulation of the handle 32.

Figure 4:
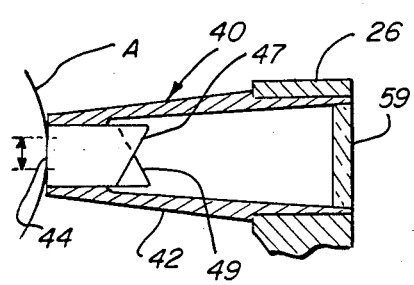
FIG. 4 is a cross sectional view reduced in size of a preferred form of the corneal applanation device, illustrated in FIGS. 1-3, suitable for use in the invention.

The corneal applanation device 40 of a preferred type used in the invention is illustrated in FIG. 4. The tubular body 42 is frictionally held in a bore 43 formed in housing 26. A partially crimped cross-shaped slit 53 formed in the housing 26 ensures the frictional fit of the tubular body 42 in the housing 26. The rear end of the tubular body 42 is sealed by means of a disc 59 of a transparent material, whereas the fore end of the tubular body 42 is sealed by means of a cylindrical body 61 of transparent material, having a corneal contact surface 44 at its outer end and two oppositely inclined prism surfaces 47 and 49 at its inner end, each of said prism surfaces covering one half of the circular face of the cylindrical body 61. The corneal contact surface 44 is illustrated in contact with a cornea A.

From the above description it is apparent that there has been brought to the art a new and improved apparatus for supporting and facilitating sterilization of the corneal contact surface of an applanation tonometer.

While only certain embodiments have been set forth, alternative embodiments and various modifications will be apparent from the above description to those skilled in the art. These and other alternatives are considered equivalents and within the scope and spirit of the present invention.

What is claimed is:

1. An apparatus facilitating sterilization of the corneal contact surface in an applanation tonometer, which comprises:
   (a) a corneal applanation device comprising a tubular body having a planar corneal contact surface at one end thereof for bearing against a cornea;
   (b) a housing for supporting said tubular body;
   (c) a base for supporting said housing;
   (d) connecting means for connecting said housing to said base and allowing said housing to pivot about said base into a sterilizing position; and
   (e) sterilization means operatively connected to the tonometer for sterilizing said corneal contact surface upon pivoting said housing about said base.

2. The apparatus of claim 1, further comprising handle means connected to said housing for grasping and pivoting said housing about said base.

3. The apparatus of claim 1 further comprising a lever, said base and said housing having an aperture formed therein permitting adjustment of the vertical position of the apparatus on said lever.

4. The apparatus of claim 1 wherein said sterilization means is a container holding a sterilizing medium.

5. The apparatus of claim 4 wherein said sterilizing medium is an oxidizing solution.

6. The apparatus of claim 5 wherein said oxidizing solution is hydrogen peroxide.

7. In an applanation tonometer for measuring intraocular pressure including a tubular corneal applanation device having a corneal contact surface at one end thereof adapted to be applied to the cornea of an eye and means cooperative therewith for transmitting and measuring the force to balance the intraocular pressure of an eye by urging the corneal contact surface against the cornea, the improvement comprising:
   (a) a hinged housing means for supporting said corneal applanation device on a lever means whereby said corneal applanation device and its associated corneal contact surface are hingedly movable between a generally horizontal measuring position and a generally vertical sterilization position; and
   (b) sterilization means operatively connected to the tonometer and in close proximity to said corneal applanation device for sterilizing said corneal contact surface, when said corneal applanation device is in said sterilization position.

8. The improvement of claim 7, wherein said sterilization means comprises an oxidizing solution.

9. The improvement of claim 8 wherein said oxidizing solution is hydrogen peroxide.

10. The improvement of claim 7, wherein said sterilizing means employs ultraviolet radiation.

11. A process for measuring intraocular pressure of an eye using an applanation tonometer, which comprises:
   (a) moving a sterilized corneal contact surface of a corneal applanation device into an intraocular measuring position;
   (b) urging said sterilized corneal contact surface against a cornea with a measured force and to a predetermined degree of applanation;

(c) withdrawing said corneal contact surface from the cornea;
(d) rotating said corneal contact surface to a depending position relative to a rotational axis; and
(e) sterilizing said corneal contact surface using sterilization means operatively connected to the tonometer, for subsequent measuring of intraocular pressure with a sterilized corneal contact surface.

* * * * *